· US009689810B2

United States Patent
Hsu et al.

(10) Patent No.: US 9,689,810 B2
(45) Date of Patent: Jun. 27, 2017

(54) ELECTRONIC APPARATUS WITH PROXIMITY SENSOR AND AUTOMATIC CALIBRATION METHOD THEREOF

(71) Applicant: HTC Corporation, Taoyuan County (TW)

(72) Inventors: Chuan-Ying Hsu, Taoyuan County (TW); Tung-Hao Hsu, Taoyuan County (TW); Chih-Hao Yan, Taoyuan County (TW)

(73) Assignee: HTC Corporation, Taoyuan (TW)

( * ) Notice: Subject to any disclaimer, the term of this patent is extended or adjusted under 35 U.S.C. 154(b) by 199 days.

(21) Appl. No.: 14/474,322

(22) Filed: Sep. 2, 2014

(65) Prior Publication Data
US 2015/0097789 A1    Apr. 9, 2015

Related U.S. Application Data

(60) Provisional application No. 61/887,998, filed on Oct. 8, 2013.

(51) Int. Cl.
*G06F 3/045* (2006.01)
*G01N 21/94* (2006.01)
*H04M 1/725* (2006.01)

(52) U.S. Cl.
CPC ........ *G01N 21/94* (2013.01); *H04M 1/72519* (2013.01); *G01N 2021/945* (2013.01); *H04M 2250/12* (2013.01)

(58) Field of Classification Search
CPC ............ G01N 21/94; G01N 2021/945; H04M 1/72519; H04M 2250/12; H04M 1/72577;
(Continued)

(56) References Cited

U.S. PATENT DOCUMENTS 8,390,597 B2 *   3/2013   Bernstein .............. G06F 3/0416
                                                      178/18.06
2007/0032967 A1    2/2007   Feen et al.
(Continued)

FOREIGN PATENT DOCUMENTS

CN    102609082 A    7/2012
CN    103123394 A    5/2013
(Continued)

OTHER PUBLICATIONS

Corresponding German Office Action that these art references were cited.
Corresponding Chinese Office Action issued on Apr. 6, 2017.

*Primary Examiner* — Nelson Rosario
(74) *Attorney, Agent, or Firm* — CKC & Partners Co., Ltd.

(57) ABSTRACT

An automatic calibration method suitable for an electronic apparatus comprising a proximity sensor is disclosed. The automatic calibration method includes steps of: resetting data comprising a minimal index and a maximal index when a specific function is activated; updating the minimal index and the maximal index according to readings from the proximity sensor; resetting the minimal index when the proximity sensor detects a far event according to a threshold value of the proximity sensor; resetting the maximal index when the proximity sensor detects a near event according to the threshold value; and, re-calculating the threshold value according to the minimal index or the maximal index every time the minimal index or the maximal index is updated.

18 Claims, 4 Drawing Sheets

(58) Field of Classification Search
CPC .. H04M 1/22; H04M 2250/22; H03K 17/941; H03K 2217/94026; H04W 52/0254; Y02B 60/50
See application file for complete search history.

(56) References Cited

U.S. PATENT DOCUMENTS

| | | | |
|---|---|---|---|
| 2009/0289914 A1* | 11/2009 | Cho | G06F 3/044 345/173 |
| 2012/0050189 A1* | 3/2012 | Choboter | H04M 1/72577 345/173 |
| 2014/0066124 A1* | 3/2014 | Novet | H04M 1/72569 455/556.1 |

FOREIGN PATENT DOCUMENTS

| | | |
|---|---|---|
| DE | 102011055862 A1 | 6/2012 |
| JP | 2005140596 A | 6/2005 |

\* cited by examiner

ELECTRONIC APPARATUS WITH PROXIMITY SENSOR AND AUTOMATIC CALIBRATION METHOD THEREOF

CROSS-REFERENCE TO RELATED APPLICATION

This application claims the priority benefit of U.S. Provisional Application Ser. No. 61/887,998, filed Oct. 8, 2013, the full disclosures of which are incorporated herein by reference.

BACKGROUND

Field of Invention

The present application relates to an automatic calibration method. More particularly, the present application relates to an automatic calibration method for a proximity sensor within an electronic apparatus.

Description of Related Art

Recently, many electronic devices (e.g., mobile phones) are equipped with touch screens. The touch screens serve as displayers for showing images or information and also as input interfaces for sensing touch events from user.

When an electronic device, such as the mobile phone, is hold adjacent to user's ear during a phone-call, the mobile phone will launch a power-saving function, such as to dim the screen down and also deactivate the touch-sensing function into a suspended mode. Switching the mobile phone into the suspended mode is able to reduce power consumption and avoid unexpected touch inputs. When the mobile phone is hold away from user's ear, the touch screen is lit up again and the user can manipulate via the touch screen at that time.

However, the touch screen fails to resume the active mode (e.g., lighting up and activating the touch-sensing function) as expected under some situations, each as the calibration of the proximity sensor of the mobile phone is failed during manufacturing, or there are some greases/dusts/stains blocking sensing area of the proximity sensor. It will be inconvenient if the touch screen fails to resume the active mode automatically.

SUMMARY

This disclosure aims to solve the problem that a touch screen of an electronic apparatus cannot resume the active mode (e.g., lighting up and activating the touch-sensing function) as expected when the electronic apparatus is moved away, by dynamically calibrating a threshold value of a proximity sensor on the electronic apparatus.

An aspect of the present disclosure is to provide an automatic calibration method which is suitable for an electronic apparatus comprising a proximity sensor. The automatic calibration method includes steps of: resetting data comprising a minimal index and a maximal index when a specific function is activated; updating the minimal index and the maximal index according to readings from the proximity sensor; resetting the minimal index when the proximity sensor detects a far event according to a threshold value of the proximity sensor; resetting the maximal index when the proximity sensor detects a near event according to the threshold value; and, re-calculating the threshold value according to the minimal index or the maximal index every time the minimal index or the maximal index is updated.

Another aspect of the present disclosure is to provide an electronic apparatus, which includes a proximity sensor and a control unit. The control unit is configured for dynamically controlling a threshold value of the proximity sensor. The control unit includes computer-executable instructions for performing a method, which include steps of: resetting data comprising a minimal index and a maximal index when a specific function is activated; updating the minimal index and the maximal index according to readings from the proximity sensor; resetting the minimal index when the proximity sensor detects a far event according to a threshold value of the proximity sensor; resetting the maximal index when the proximity sensor detects a near event according to the threshold value; and, re-calculating the threshold value according to the minimal index or the maximal index every time the minimal index or the maximal index is updated.

BRIEF DESCRIPTION OF THE DRAWINGS

The disclosure can be more fully understood by reading the following detailed description of the embodiments, with reference made to the accompanying drawings as follows.

DETAILED DESCRIPTION

Figure 1:
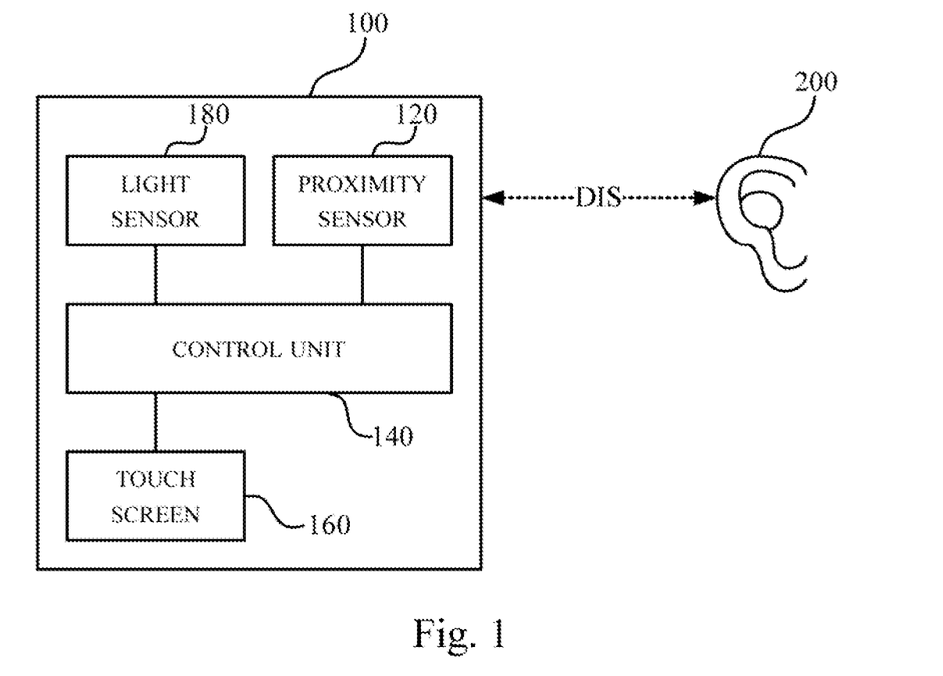
FIG. 1 is a schematic diagram illustrating an electronic apparatus according to an embodiment of the disclosure.

Reference is made to FIG. 1 which is a schematic diagram illustrating an electronic apparatus 100 according to an embodiment of the disclosure. As shown in FIG. 1, the electronic apparatus 100 includes a proximity sensor 120, a control unit 140 and a touch screen 160. In this embodiment, the electronic apparatus 100 further includes a light sensor 180.

The proximity sensor 120 is utilized to provide a reading which indicates a distance DIS between an external object 200 (e.g., user's ear in the embodiment of FIG. 1) and the electronic apparatus 100. In other words, the proximity sensor 120 is utilized to determine how close it is between the electronic apparatus 100 and the object 200. In practical applications the object 200 is not only limited to user's ear, and can be any object located in front of a sensing area of the proximity sensor 120.

Figure 2:
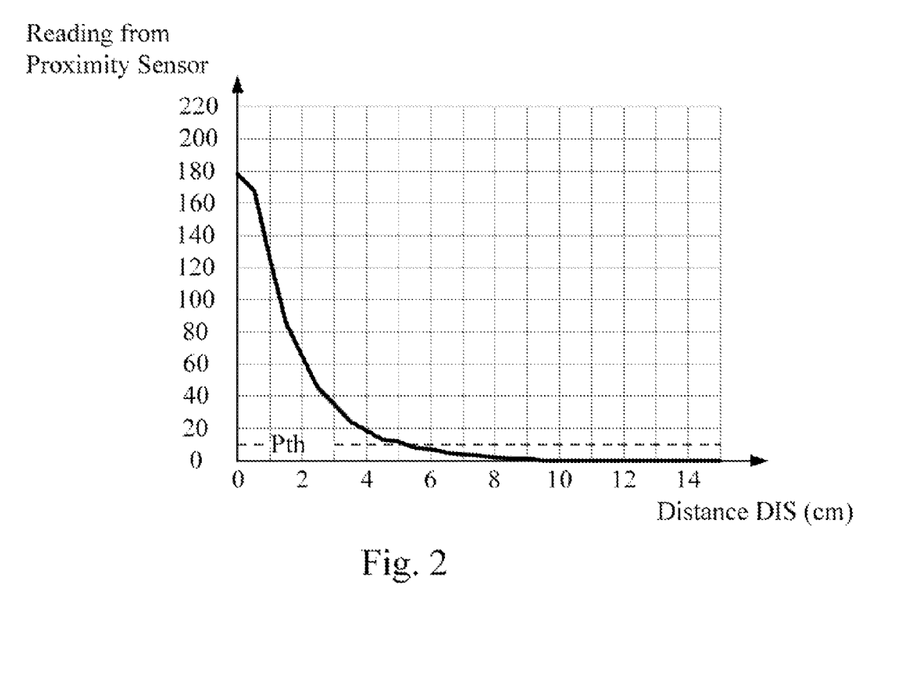
FIG. 2 is a line chart illustrating a relationship between the reading from the proximity sensor and the distance according to an embodiment of the disclosure.

Reference is also made to FIG. 2, which is a line chart illustrating a relationship between the reading from the proximity sensor 120 and the distance DIS according to an embodiment of the disclosure. As shown in FIG. 2, the proximity sensor 120 provides different readings under different distances DIS (between the external object 200 and the electronic apparatus 100).

A current reading from the proximity sensor 120 reflects the distance DIS currently. For example, the current reading from the proximity sensor 120 shown in FIG. 2 increases when the distance DIS is closer. On the other hand, the current reading decreases when the distance DIS is larger. The reading from the proximity sensor 120 is compared with a threshold value Pth of the proximity sensor 120 for detecting a far event or a near event. In this case, the far event is detected when the current reading is below or equal to the threshold value Pth (i.e., the reading≤Pth), and the near event is detected when the current reading exceeds the threshold value Pth (i.e., the reading>Pth).

In another embodiment, the reading from the proximity sensor 120 is compared with a far threshold value PthF and a near threshold value PthN. In this case, the far event is detected when the current reading is below or equal to the threshold value PthF (i.e., the reading≤PthF). The near event is detected when the current reading exceeds or equal to the near threshold value PthN (i.e., the reading≥PthN). In this embodiment, the far threshold value PthF and the near threshold value PthN can be set as: PthN=PthF+1. In this case, the far threshold value PthF is utilized to trigger the far event, and the near threshold value PthN is utilized to trigger the near event.

In the following paragraphs for demonstrating this disclosure in a simple way, the threshold value Pth is utilized to a reference standard to trigger the near event and the far event alternatively. However, the disclosure is not limited to only one threshold value. The threshold value Pth in the following paragraphs can be replaced by two threshold values such as the far threshold value PthF and the near threshold value PthN in aforesaid case.

In an embodiment, the threshold value Pth (or the far threshold value PthF and the near threshold value PthN) can be stored in a register of the proximity sensor 120, a register of the control unit 140, a register of a processor (no shown) of the electronic apparatus 100, or a memory unit (no shown) of the electronic apparatus 100.

In some embodiments shown as FIG. 2, the current reading from the proximity sensor 120 is negatively correlated to the distance DIS (i.e., the reading increases when the distance is closer; the reading decreases when the distance is larger), but this disclosure is not limited thereto.

In other embodiments, the current reading from the proximity sensor 120 is positively correlated to the distance DIS (the current reading increases when the distance DIS is larger; the current reading decreases when the distance is closer). In this specific case, the far event is detected when the current reading exceeds the threshold value, and the near event is detected when the current reading is below the threshold value. It is know by a person in the art to alternate these two logics (the negative correlation and the positive correlation) on the proximity sensor 120 and re-design accordingly. In order to simply the following explanations, the reading from the proximity sensor 120 is negatively correlated to the distance DIS for demonstrating.

As the example shown in FIG. 2, the reading from the proximity sensor 120 is compared with the threshold value Pth "10" in this example for detecting the far event or the near event. In this case, the far event is detected when the current reading is below the threshold value Pth (i.e., the current reading≤10), and the near event is detected when the current reading exceeds the threshold value Pth (i.e., the current reading>10). The threshold value must be set at a proper value to make sure that the proximity sensor 120 can detect both of the near event and the far event without being oversensitive.

There is a practical manner to calibrate the threshold value. A relative minimal reading of the proximity sensor is refreshed once after a phone-call started. The threshold value is calculated according to the relative minimal reading. For example, when the relative minimal reading is "0", the threshold value is set to be "10" (the relative minimal reading "0"+a compensation value "10"=the threshold value "10"); when the relative minimal reading is "5", the threshold value is set to be "15" (the minimal reading "5"+a compensation value "10"=the threshold value "15"), etc.

The threshold value is utilized for triggering the operation of turning on/off the touch screen 160 (or display screen) and also activating/deactivating the touch-sensing function. In some embodiment, a backlight of the touch screen 160 can be lit up when the touch screen 160 is turned on; and the backlight of the touch screen 160 can be dimmed down when the touch screen 160 is turned off. In the practical manner, once the relative minimal reading is found and settled down related to one phone-call, the threshold value is set and will no longer be updated during the same phone-call.

If the user move the electronic apparatus closer to his ear and inadvertently stain/soil/block the surface of the proximity sensor and the affection of the stain is greater than the threshold value calculated based on the relative minimal reading, the proximity sensor cannot properly trigger the far event when the electronic apparatus is actually moved away from user, such that the touch screen cannot switch into the active mode properly (lighting up and/or activating the touch-sensing function).

If user holds the electronic apparatus near and an intense glare is projected to the electronic apparatus at that time, the relative minimal reading of the proximity sensor will be extraordinary low due to the intense glare. A new threshold value (which will be low than normal value) is calculated according to the relative minimal reading affected by the intense glare. When user walks away from the glare and moves the electronic apparatus away from his ear, the reading of the proximity sensor will resume to its ordinary value. If the ordinary value of the proximity sensor is still larger than the threshold value calculated under the glare, the proximity sensor cannot trigger the far event, such that the touch screen cannot switch into the active mode properly (lighting up and/or activating the touch-sensing function).

Figure 3:
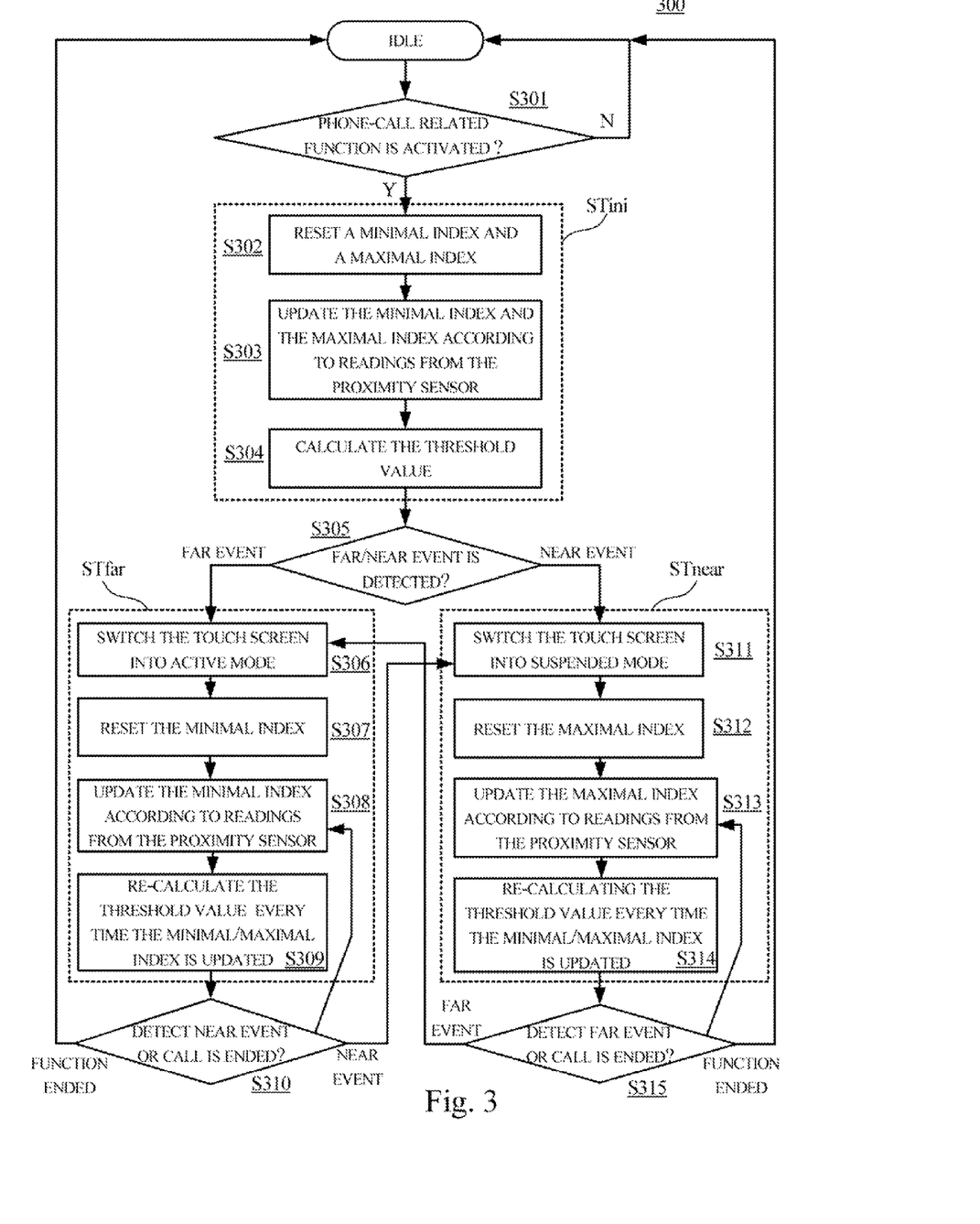
FIG. 3 is a flow-chart diagram illustrating an automatic calibration method according to an embodiment of this disclosure.

The control unit 140 is utilized for dynamically controlling a threshold value of the proximity sensor, so as to avoid aforesaid problems (e.g., the proximity sensor cannot trigger the far event due to an improper threshold value). In this embodiment, the control unit 140 includes computer-executable instructions for performing an automatic calibration method. Reference is also made to FIG. 3, which is a flow-chart diagram illustrating an automatic calibration method 300 according to an embodiment of this disclosure.

As shown in FIG. 3, the automatic calibration method 300 will be triggered when user activate a specific function. In the embodiment, the specific function includes a phone-call related function (e.g., picking up an incoming phone call, making a phone call on the electronic apparatus, launching a specific application or enabling a specific function of an application). Step S301 is executed to determine if the phone-call related function is activated. When there is no phone-call related function being activated, the electronic apparatus 100 is in a standby mode or an operational mode if the user manipulates other functions on the electronic device 100. When the phone-call related function is activated (e.g. picking up or making a phone call), step S302 is executed for resetting data including a minimal index and a maximal index. The data, DATA [min, max], is utilized to register a minimal reading and a maximal reading from the proximity sensor 120 since the phone-call related function is activated.

In an exemplary case adopting 8-digits storage (e.g., ranged from "0" to "255") for each index, the DATA [min, max] is refreshed into DATA[255, 0] or DATA[NULL, NULL] in step S302. In other words, the minimal index is reset to "255" or "NULL", and the maximal index is reset to "0" or "NULL" right after the phone-call related function is activated.

Then, step S303 is executed for updating the minimal index and the maximal index according to readings from the proximity sensor 120. In further details, the step S303 of updating the minimal index and the maximal index is completed by monitoring a current reading from the proximity sensor 120 periodically and comparing the current reading to both of the minimal index and the maximal index. The current reading indicates a distance between an object and the electronic apparatus currently (as shown in FIG. 2). When the current reading is below the minimal index, the minimal index is updated to be equal to the current reading. On the other hand, when the current reading exceeds the maximal index, the maximal index is updated to be equal to the current reading.

It is noticed that, the monitoring procedure (monitoring the reading from the proximity sensor 120 periodically and updating the DATA [min, max]) is activated since the phone-call related function is activated until the function is terminated, such that the DATA [min, max] can maintain the minimal reading and the maximal reading from the proximity sensor 120 in real-time.

Step S304 is executed to calculate the threshold value (referring to the threshold value Pth in aforesaid embodiments and FIG. 2) corresponding to the proximity sensor 120. The threshold value is utilized as a reference standard to be compared with reading from the proximity sensor 120 for detecting the far event or the near event.

In an exemplary case, when the phone-call related function is just activated (e.g., picking up or making a phone call), the DATA [min, max] is refreshed into DATA[255, 0] in step S302. Afterward, the DATA [min, max] is updated into DATA[0, 13] in step S303 in the exemplary case (because user may hold the electronic apparatus 100 away to see who is calling, or to dial the numbers on the touch screen 160). Afterward, the threshold value is set to "10" according to the minimal index (the threshold value "10"=the minimal index "0"+a compensation value "10"). Aforesaid steps S302, S303 and S304 are regarded as an initial state STini of the automatic calibration method 300 to set up an initial threshold value.

Afterward, step S305 is executed for detecting the far event or the near event according to the threshold value set in step S304. If the proximity sensor 120 detects the far event, the automatic calibration method 300 enters a far state STfar. On the other hand, when the proximity sensor 120 detects the near event, the automatic calibration method 300 enters a near state STnear.

In the far state STfar, i.e., the proximity sensor 120 detects the far event, step S306 is executed for switching the touch screen 160 in an active mode by the control unit 140. For example, the touch screen 160 is lit up and the touch-sensing function of the touch screen 160 is activated in the active mode.

Step S307 is executed for resetting the minimal index. For example, the minimal index is reset to "255" or "NULL". Afterward, step S308 is executed for updating the minimal index (and the maximal index if necessary) according to readings from the proximity sensor 120. In this situation of the far state STfar (i.e., the current reading from the proximity sensor 120 is smaller than threshold value), it is more likely to find a new minimal index for updating the current minimal index. The detail behavior of step S308 for updating the minimal index and/or the maximal index is similar to step S303, and not to be repeated herein.

Every time the minimal index or the maximal index is updated (once a new minimal/maximal index is found), Step S309 is executed for re-calculating the threshold value according to the updated minimal index or the updated maximal index.

The original minimal index set up previously (e.g., in step S303) is discarded by step S307, and the minimal index is re-assigned by step S308, such that the minimal index is updated in the far state STfar. Accordingly, the threshold value is recalculated (at least once) in step S309 according to the updated minimal index, such that the threshold value will be suitable for the present situation of the electronic apparatus 100.

Once a new minimal/maximal index is found, step S309 is executed to re-calculate the threshold value. Aforesaid, step S310 is executed for detecting the near event or if the phone-call related function is ended. If proximity sensor 120 detects the near event, the automatic calibration method 300 enters the near state STnear; if the phone-call related function is ended, the electronic apparatus 100 returns to the idle mode; otherwise, when the phone remains to executes the phone-call related function and remains in the far state STfar (without detecting the near event), steps S308 and S309 are repeatedly executed in the far state STfar.

In the near state STnear, i.e., the proximity sensor 120 detects the near event, step S311 is executed for switching the touch screen 160 in a suspended mode by the control unit 140. For example, the touch screen 160 is dimmed down (or turned off) and the touch-sensing function of the touch screen 160 is deactivated in the suspended mode.

Step S312 is executed for resetting the maximal index. For example, the maximal index is reset to "0" or "NULL". Afterward, step S313 is executed for updating the maximal index (and the minimal index if necessary) according to readings from the proximity sensor 120. In this situation of the near state STnear (i.e., the current reading from the proximity sensor 120 is larger than threshold value), it is more likely to find a new maximal index for updating the current maximal index. The detail behavior of step S313 for updating the minimal index and the maximal index is similar to step S303, and not to be repeated herein.

Every time the minimal index or the maximal index is updated (once a new minimal/maximal index is found), Step S314 is executed for re-calculating the threshold value according to the updated minimal index or the updated maximal index.

The original maximal index set up previously is discarded by step S312, and the maximal index is re-assigned by step S313, such that the maximal index is updated in the near state STnear. Accordingly, the threshold value is recalculated (at least once) in step S314 according to the minimal index or the maximal index, such that the threshold value will be suitable for the present situation of the electronic apparatus 100.

Once a new minimal/maximal index is found, step S314 is executed to re-calculate the threshold value. Aforesaid, step S315 is executed for detecting the far event or if the phone-call related function is ended. If proximity sensor 120 detects the far event, the automatic calibration method 300 enters the near state STnear; if the phone-call related function is ended, the electronic apparatus 100 returns to the idle mode; otherwise, when the phone remains to executes the phone-call related function and remains in the near state STnear (without detecting the far event), steps S313 and S314 are repeatedly executed in the near state STnear.

Figure 4:
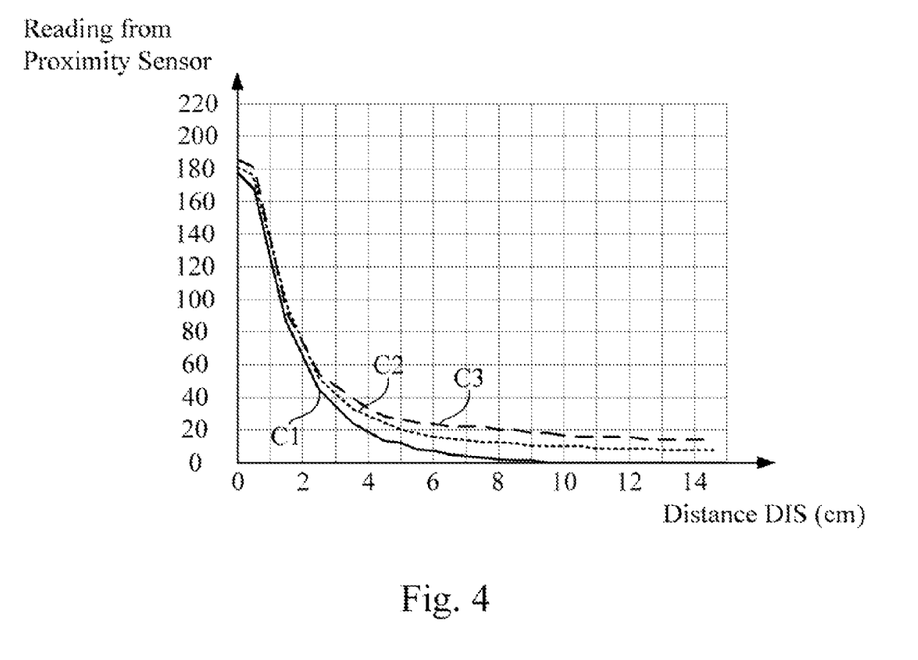
FIG. 4 is a line chart illustrating relationship curves between the reading from the proximity sensor and the distance under different grease levels according to an embodiment of the disclosure.

Reference is also made to FIG. 4, which is a line chart illustrating relationship curves C1/C2/C3 between the reading from the proximity sensor 120 and the distance DIS under different grease levels according to an embodiment of the disclosure. As shown in FIG. 4, when the proximity sensor 120 is affected by greases, dusts, or stains blocking sensing area of the proximity sensor 120 at different levels, the readings of the proximity sensor 120 follows different curves C1/C2/C3. For example, the curve C1 represents the condition when the proximity sensor 120 is not affected by the greases, dusts, or stains; the curve C2 represents the condition when the proximity sensor 120 is less affected; the curve C3 represents the condition when the proximity sensor 120 is deeply affected.

When user talks on the phone, it is possible that the proximity sensor 120 is affected by the greases, dusts, or stains during the phone-call. If the threshold value is fixed at "10" and not dynamically updated, the proximity sensor 120 under the grease level corresponding to the curve C3 will never detect the far event. In present disclosure, the threshold value will be re-calculated dynamically during the phone-call at each time the minimal index or the maximal index is updated. For example, actions such as moving the electronic apparatus 100 toward user, moving the electronic apparatus 100 away from user, or related readings/sensing signals of aforesaid movement (readings of sensors, interrupt events, etc) are able to trigger the operation for re-calculating the threshold value of the proximity sensor 120.

According to aforesaid embodiments, the minimal index will be re-set from time to time, such that the threshold value is dynamically re-calculated and updated (triggered by new minimal or new maximal index is found) during the phone-call, such that the threshold value will not be fixed at improper value during the whole phone-call.

According to aforesaid embodiments, Steps S303, S308 and S313, the minimal index is updated to be equal to the current reading when the current reading of the proximity sensor 120 is below the minimal index. However, the disclosure is not limited thereto. In some other embodiments, the minimal index is updated to be equal to the current reading only when two conditions are satisfied. The first condition is that a sum of the current reading and a light sensor correction value is below the minimal index, e.g., [the current reading+a light sensor correction value<the current minimal index]. The second condition is that a difference between a previous reading of the proximity sensor and the current reading is within a predetermined gap, e.g., [the previous reading of the proximity sensor—the current reading of the proximity sensor<the predetermined gap "10"].

The first condition is able to avoid the frequently amending the minimal index by small difference, such as the current reading is "39" and the present minimal index is "40", and this updating to the minimal index leads to small difference (or almost no difference) to the threshold value. The second condition is able to avoid the transient error of the current reading. If the current reading varies significantly from the previous reading in a sudden, the current reading is regarded as an error reading and ignored by the second condition.

In some other embodiments, the threshold value is set according to the calculation outcome only if the calculation outcome is smaller than a predetermined value such as 66, so as to avoid the proximity sensor 120 being too sensitive.

According to aforesaid embodiments, Steps S309 and S314, the threshold value is re-calculated according to the minimal index every time either the minimal index or the maximal index is updated. However, the disclosure is not limited thereto. In some other embodiments, if the minimal index is "0", the threshold value will be set to "10" by adding a correction (evaluated by the distance DIS as shown in FIG. 2 and FIG. 4) for grease levels on the proximity sensor 120. The distance DIS is smaller (i.e., the object 200 is closer), the more correction will be added.

If the condition is satisfied that:

[the current maximal index−180+the correction]<[the current minimal index+the correction], and it means the electronic apparatus 100 is under a normal condition. Under the normal condition, the control unit 140 sets the threshold value to be [the current minimal index+the correction].

In the relationship that [the current maximal index−180+the correction]<[the current minimal index+the correction], the "180" is a common/regular reading value generated by the proximity sensor 120 when an object is located adjacent to the proximity sensor 120 (as in the embodiment shown in FIG. 4, the reading value of the proximity sensor 120 is substantially ranged from 0 to 200). For example, when a paper (for simulating an object) is moved toward and located in front of the proximity sensor 120, the reading value of the proximity sensor 120 will approximately be "180".

Under a normal condition (the proximity sensor 120 is working properly, not damaged, not affected by an obstacle, etc), [the current maximal index−180+the correction] will be less than [the current minimal index+the correction]. In the normal case, the control unit 140 sets the threshold value to be [the current minimal index+the correction].

In addition, under the normal condition, [the current minimal index+the correction] is the lower boundary of the threshold value for detecting the near event. In the equation, "the correction" indicates a tolerance windows for detecting the far event. If "the correction" is larger, the tolerance windows of the far event is larger, i.e., easier to be determined as the far event.

Otherwise, if another condition is satisfied that:

[the current maximal index−180+the correction]≥ [current minimal index+rection], and, it means the p-sensor is not working properly (the proximity sensor might be damaged, affected by an obstacle, or suffered some abnormal conditions), the control unit 140 sets the threshold value to [the current maximal index−180+the correction].

In the relationship that [the current maximal index−180+the correction]≥[the current minimal index+the correction], it means the current maximal index is unexpectedly larger than the common/regular reading value "180" under the near event. For example, the current maximal index might be 230 in this case to satisfy this condition. It indicates that the proximity sensor 120 is currently generating an abnormal reading larger than the regular case. If the threshold value is still set according to the [the current minimal index+the correction] e.g. the threshold value=10, the threshold value will be too small, the reading from the proximity sensor 120 will always be larger than the threshold value, and the far event will never be triggered. Therefore, in this abnormal condition, the control unit 140 sets the threshold value to [the current maximal index−180+the correction]. In other words, in Steps S309 and S314, the threshold value is re-calculated according to the maximal index in this case in this abnormal condition (i.e., [the current maximal index−180+the correction]≥[current minimal index+correction]).

Based on aforesaid embodiments, Steps S309 and S314 in this disclosure are performed for re-calculating the threshold value according to the maximal index and/or the minimal index.

In aforesaid conditions, the bigger one between [the current maximal index−180+the correction] and [current minimal index+correction] is served as the threshold value, such that the far event can be triggered properly under the normal condition and the abnormal condition.

Additionally, the automatic calibration method 300 according to the disclosure also provides a manner to reduce the effect by an intense glare to the proximity sensor 120. As shown in FIG. 1, the electronic apparatus 100 further includes the light sensor 180. The light sensor 180 is utilized for providing a light sensor reading. Therefore, Steps S309 and S314 for re-calculating the threshold value in this disclosure further includes following steps.

Firstly, the light sensor reading from the light sensor is compared with a predetermined intense glare constant (e.g., 0x1500). If the light sensor reading is below the predetermined intense glare constant, the threshold value is set to be a sum of the minimal index and a fixed value (e.g., "10" or aforesaid light sensor correction value). If the light sensor reading exceeds the intense glare constant, the threshold value is set to be a sum of the minimal index and an intense glare compensation value. The intense glare compensation value (e.g., "30"~"40") is larger than the fixed value.

Based on aforesaid embodiment, the minimal index will be re-set from time to time, such that the threshold value is dynamically re-calculated and updated (triggered by new minimal or new maximal index is found) during the phone-call, such that the threshold value will not be fixed at improper value during the whole phone-call.

It will be apparent to those skilled in the art that various modifications and variations can be made to the structure of the present application without departing from the scope or spirit of the application. In view of the foregoing, it is intended that the present application cover modifications and variations of this application provided they fall within the scope of the following claims.

What is claimed is:

1. An automatic calibration method, suitable for an electronic apparatus comprising a proximity sensor, the automatic calibration method comprising:
   resetting data comprising a minimal index and a maximal index when a specific function is activated;
   updating the minimal index and the maximal index according to readings from the proximity sensor;
   resetting the minimal index when the proximity sensor detects a far event according to at least one threshold value of the proximity sensor;
   resetting the maximal index when the proximity sensor detects a near event according to the threshold value; and
   re-calculating the threshold value according to the minimal index or the maximal index every time the minimal index or the maximal index is updated,
   wherein step of updating the minimal index and the maximal index comprises:
      monitoring a current reading from the proximity sensor periodically, the current reading indicating a distance between an object and the electronic apparatus currently;
      comparing the current reading to both of the minimal index and the maximal index; and
      updating the minimal index to be equal to the current reading only when a sum of the current reading and a light sensor correction value is below the minimal index and also a difference between a previous reading of the proximity sensor and the current reading is within a predetermined gap.

2. The automatic calibration method of claim 1, wherein step of updating the minimal index and the maximal index further comprises:
   updating the maximal index to be equal to the current reading when the current reading exceeds the maximal index.

3. The automatic calibration method of claim 2, wherein the current reading increases when the distance is closer, the current reading decreases when the distance is larger, the far event is detected when the current reading is below the threshold value, and the near event is detected when the current reading exceeds the threshold value.

4. The automatic calibration method of claim 2, wherein the current reading increases when the distance is larger, the current reading decreases when the distance is closer, the far event is detected when the current reading exceeds the threshold value, and the near event is detected when the current reading is below the threshold value.

5. The automatic calibration method of claim 1, wherein the electronic apparatus further comprises a touch screen, when the proximity sensor detects the near event, the automatic calibration method further comprising:
   dimming down the touch screen; and
   deactivating a touch-sensing function of the touch screen.

6. The automatic calibration method of claim 1, wherein the electronic apparatus further comprises a touch screen, when the proximity sensor detects the far event, the automatic calibration method further comprising:
   lighting up the touch screen; and
   activating a touch-sensing function of the touch screen.

7. The automatic calibration method of claim 1, the specific function comprises launching or answering a phone call on the electronic apparatus.

8. The automatic calibration method of claim 1, wherein the electronic apparatus further comprises a light sensor, at each time the minimal index is updated, the step of re-calculating the threshold value comprises:
   comparing a light sensor reading from the light sensor with an intense glare constant;
   if the light sensor reading is below the intense glare constant, the threshold value is set to be a sum of the minimal index and a fixed value; and
   if the light sensor reading exceeds the intense glare constant, the threshold value is set to be a sum of the minimal index and an intense glare compensation value, the intense glare compensation value is larger than the fixed value.

9. The automatic calibration method of claim 1, wherein at each time the maximal index is updated, the step of re-calculating the threshold value comprises:
   determining whether the proximity sensory is affected because of a grease or a stain by comparing the maximal index with the minimal index;
   if the proximity sensory is affected, the threshold value is set to be the maximal index with a deduction value; and
   if the proximity sensory is not affected, the threshold value is set to be a sum of the minimal index and a fixed value.

10. An electronic apparatus, comprising:
   a light sensor;
   a proximity sensor; and
   a control unit, for dynamically controlling a threshold value of the proximity sensor, wherein the control unit comprises computer-executable instructions for performing a method, comprising:
      resetting data comprising a minimal index and a maximal index when a specific function is activated;

updating the minimal index and the maximal index according to readings from the proximity sensor;

resetting the minimal index when the proximity sensor detects a far event according to a threshold value of the proximity sensor;

resetting the maximal index when the proximity sensor detects a near event according to the threshold value; and re-calculating the threshold value according to the minimal index or the maximal index every time the minimal index or the maximal index is updated, wherein step of updating the minimal index and the maximal index comprises:

monitoring a current reading from the proximity sensor periodically, wherein the current reading indicates a distance between an object and the electronic apparatus currently;

comparing the current reading to both of the minimal index and the maximal index; and updating the minimal index to be equal to the current reading only when a sum of the current reading and a light sensor correction value from the light sensor is below the minimal index and also a difference between a previous reading of the proximity sensor and the current reading is within a predetermined gap.

11. The electronic apparatus of claim 10, wherein step of updating the minimal index and the maximal index further comprises:

updating the maximal index to be equal to the current reading when the current reading exceeds the maximal index.

12. The electronic apparatus of claim 11, wherein the current reading increases when the distance is closer, the current reading decreases when the distance is larger, the far event is detected when the current reading is below the threshold value, and the near event is detected when the current reading exceeds the threshold value.

13. The electronic apparatus of claim 11, wherein the current reading increases when the distance is larger, the current reading decreases when the distance is closer, the far event is detected when the current reading exceeds the threshold value, and the near event is detected when the current reading is below the threshold value.

14. The electronic apparatus of claim 10, wherein the electronic apparatus further comprises a touch screen, when the proximity sensor detects the near event, the touch screen is dimmed down and a touch-sensing function of the touch screen is deactivated.

15. The electronic apparatus of claim 10, wherein the electronic apparatus further comprises a touch screen, when the proximity sensor detects the far event, the touch screen is lit up and a touch-sensing function of the touch screen is activated.

16. The electronic apparatus of claim 10, the specific function comprises launching or answering a phone call on the electronic apparatus.

17. A non-transitory computer readable storage medium, containing instructions for performing a method comprising:

resetting data comprising a minimal index and a maximal index when a specific function is activated;

updating the minimal index and the maximal index according to readings from a proximity sensor;

resetting the minimal index when the proximity sensor detects a far event according to a threshold value of the proximity sensor;

resetting the maximal index when the proximity sensor detects a near event according to the threshold value; and re-calculating the threshold value according to the minimal index or the maximal index every time the minimal index or the maximal index is updated, wherein step of updating the minimal index and the maximal index comprises:

monitoring a current reading from the proximity sensor periodically, the current reading indicating a distance between an object and the proximity sensor currently;

comparing the current reading to both of the minimal index and the maximal index; and updating the minimal index to be equal to the current reading only when a sum of the current reading and a light sensor correction value is below the minimal index and also a difference between a previous reading of the proximity sensor and the current reading is within a predetermined gap.

18. The non-transitory computer readable storage medium of claim 17, wherein the method further comprising:

when the proximity sensor detects the near event, the automatic calibration, dimming down a touch screen and deactivating a touch-sensing function of the touch screen; and when the proximity sensor detects the far event, lighting up the touch screen and activating a touch-sensing function of the touch screen.

* * * * *